United States Patent
Sugden et al.

(10) Patent No.: US 7,066,255 B2
(45) Date of Patent: Jun. 27, 2006

(54) PROTECTION AGAINST LOSS OF DOWNHOLE TOOLS

(75) Inventors: Daryl R. Sugden, Innisfail (CA); Allan Lewin, Spring Brook (CA)

(73) Assignee: Nabors Industries, Inc., Houston, TX (US)

(*) Notice: Subject to any disclaimer, the term of this patent is extended or adjusted under 35 U.S.C. 154(b) by 140 days.

(21) Appl. No.: 10/688,158

(22) Filed: Oct. 17, 2003

(65) Prior Publication Data

US 2004/0089447 A1 May 13, 2004

(51) Int. Cl.
*E21B 44/00* (2006.01)
(52) U.S. Cl. .................................. 166/250.01
(58) Field of Classification Search ........... 166/250.01, 166/54.5, 65.1, 66
See application file for complete search history.

(56) References Cited

U.S. PATENT DOCUMENTS

| | | | | |
|---|---|---|---|---|
| 1,214,709 A | 2/1917 | Orr | ........................... | 403/275 |
| 1,496,142 A | 6/1924 | Wirkkala | .................... | 403/274 |
| 4,395,798 A | 8/1983 | McVey | ...................... | 24/122.6 |
| 4,760,327 A * | 7/1988 | Walsh et al. | .................. | 324/66 |
| 5,119,874 A | 6/1992 | Ferguson et al. | ........ | 166/105.2 |
| 5,136,755 A | 8/1992 | Shaw | ........................ | 24/122.6 |
| 5,539,960 A | 7/1996 | Vanasse et al. | ............ | 24/122.6 |
| 5,553,669 A | 9/1996 | Trainer | .................... | 166/105.1 |
| 5,760,590 A * | 6/1998 | Striffler | ...................... | 324/514 |
| 6,145,590 A | 11/2000 | Havard | .................... | 166/105.2 |
| 6,619,390 B1 | 9/2003 | Kellett, III | ............... | 166/105.1 |
| 6,686,746 B1 * | 2/2004 | Allan et al. | ................. | 324/533 |

OTHER PUBLICATIONS

Bourgoyne Jr. et al, "Applied Drilling Engineering", 1986, pp. 8-12.*
H. Bogart; B. Jacobs; K. MacPhail, M. Malone, G. Sonnleitner; "Testing of Wire Rope Socket"; Engineering Science Laboratories, Montana Tech, May 2, 1984.
Bruce Levan; "Preliminary Analysis of a Sand Line"; Canspec Group Inc., Jul. 6, 1992.
David R. Hall; "Electromagnetic Inspection of Wire Ropes Vertical Lift Bridges", Jun. 2002.

* cited by examiner

*Primary Examiner*—Frank S. Tsay
(74) *Attorney, Agent, or Firm*—Baker Botts L.L.P.

(57) ABSTRACT

A method of protecting against loss of downhole tools in wells, the method comprising the steps of making repeated use of a wire rope to suspend downhole tools in wells, the downhole tools being suspended from a downhole end of the wire rope, testing the integrity of the wire rope from time to time according to a maintenance schedule, and shortening the wire rope when the wire rope fails integrity testing. Tests that may be performed are a test of the longitudinal strength of at least one wire from the downhole end of the wire rope, a test of the stretch of the wire rope, a test of the diameter of a wire from the downhole end of the wire rope, a test of the diameter of the downhole end of the wire rope, a test of the flex strength of a wire from the wire rope, a test of the twist strength of a wire from the wire rope; and a test of the weight of a segment of the wire rope.

23 Claims, 1 Drawing Sheet

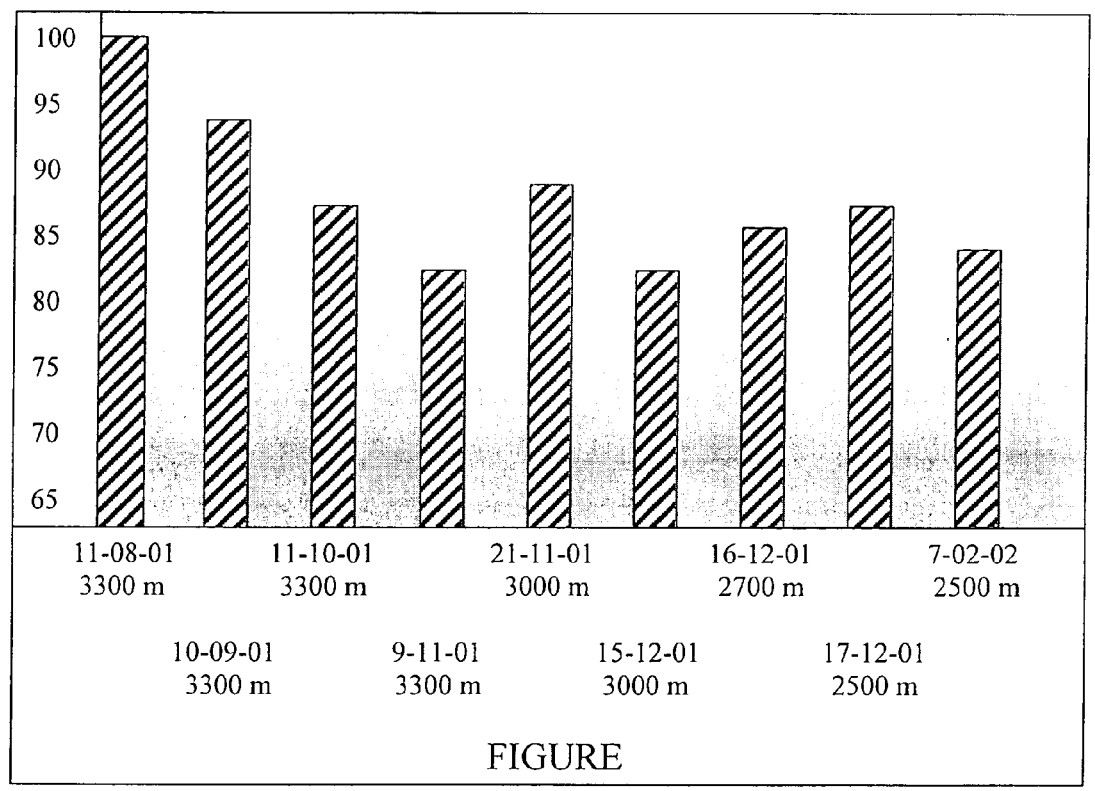
FIGURE

PROTECTION AGAINST LOSS OF DOWNHOLE TOOLS

BACKGROUND OF THE INVENTION

This invention relates to methods used for the protection against loss of equipment suspended on wire ropes, particularly as used in the swabbing of oil and gas wells.

Swabbing tools and other downhole equipment are often lowered into wells using wire ropes. The wire ropes suffer wear from chaffing on the wellbore and other equipment, corrosion from corrosive downhole fluids and destruction due to $H_2S$ embrittlement. The wire ropes frequently break due to the wear and corrosion. In a reasonably sized swabbing unit fleet, one swabbing tool can be lost downhole each week. Thus, there is a need for protecting against loss of downhole equipment. The present invention is intended to meet that need.

SUMMARY OF THE INVENTION

Therefore, according to an aspect of the invention, there is provided a method of protecting against loss of downhole tools in wells, the method comprising the steps of making repeated use of a wire rope to suspend downhole tools in wells, the downhole tools being suspended from a downhole end of the wire rope, testing the integrity of the wire rope from time to time according to a maintenance schedule, and shortening the wire rope when the wire rope fails integrity testing.

Testing the integrity of the wire rope may comprise performing a test selected from the group consisting of:

a visual test of corrosion damage;

a visual test for broken wires in the wire rope;

a test of the longitudinal strength of at least one wire from the wire rope;

a test of the stretch of the wire rope;

a test of the diameter of a wire from the wire rope;

a test of the diameter of the wire rope;

a test of the flex strength of a wire from the wire rope;

a test of the twist strength of a wire from the wire rope; and a test of the weight of a segment of the wire rope.

One or more, but preferably all, of these tests are carried out and the wire rope is shortened when the wire rope fails any one of the tests of the integrity of the wire rope. The wire rope may be shortened when the wire rope fails a test based oil more than one of the plural tests of the integrity of the wire rope. In a typical test, the wire rope is shortened when a measure of a characteristic of the wire rope is less than a pre-selected percentage of a measure of the same characteristic of a new wire rope of the same type. The tests are performed regularly, preferably monthly.

BRIEF DESCRIPTION OF THE DRAWINGS

There will now be described preferred embodiments of the invention, with reference to the drawings, by way of illustration only and not with the intention of limiting the scope of the invention, in which the sole FIGURE shows a graphical summary of wire rope inspection data.

DETAILED DESCRIPTION OF PREFERRED EMBODIMENTS

In this patent document, "comprising" means "including". In addition, a reference to an element by the indefinite article "a" does not exclude the possibility that more than one of the element is present.

In a preferred method of the invention, multiple tests are performed on a regular, and preferably monthly, schedule of the integrity of a wire rope that has been used repeatedly to suspend downhole tools in wells. The results of the tests are recorded on an inspection log. Since the wire rope generally is kept on a drum, with the downhole end outermost, the tests of integrity are performed on the downhole end of the wire rope. It is this end of the wire rope that is subject to the most corrosive conditions downhole. When the wire rope fails a test of integrity, enough of the downhole end of the wire rope is cut off to leave the remainder of the wire rope in a condition that would pass integrity testing.

Preferably, testing the integrity of the wire rope involves performing multiple tests of the integrity of the wire rope, and recording the results in an inspection log. The log includes the name of the supplier of the wire rope, the manufacturer name, the date when the wire rope was placed in service, the rig with which the wire rope is used (to identify the particular wire rope), the type of wire rope (for example, 14.30 mm, 5×7 RRL PC wire rope), the original length and the remaining length at the time of integrity testing. The wire rope is preferably shortened when the wire rope fails any one of the plural tests of the integrity of the wire rope. In addition, the wire rope is preferably shortened when the wire rope fails a test based on more than one test of the integrity of the wire rope. In a typical test, the wire rope is shortened when a measure of a characteristic of the wire rope is less than a pre-selected percentage of a measure of the same characteristic of a new wire rope of the same type. The pre-selected percentage depends on a balance between losing wire rope and losing downhole tools. Fishing downhole tools is expensive, while wire rope is cheap. Therefore, the pre-selected percentage for a typical test at which the wire rope is shortened should be set at quite a high level. The amount of wire rope removed is at a minimum the portion of rope tested, and may include additional parts of the wire rope that appear to have the same level of wear. Other portions of the wire rope may be tested if they appear suspect, and the tests described here can be applied to any portion of the wire rope that appears corroded or worn.

In a first test of the integrity of the wire rope, the wire rope is inspected for obvious deficiencies, for example a broken strand of wire or severe corrosion damage. Visual inspection alone might dictate shortening the wire rope. A broken strand itself is sufficient to require shortening of the wire rope. Corrosion damage may be rated on a relative scale for example light, medium and heavy. Heavy damage requires shortening of the wire rope. Medium damage requires careful monitoring of the wire rope. Light damage may be permitted.

In a second test of integrity, the minimum and maximum diameter of a randomly selected section of the downhole end of the rope is measured, as for example with an electronic caliper. These values are recorded and compared with the minimum and maximum diameter of the same wire rope in new condition. If the new values for the wire rope under test are not known, then the as-new values may be determined from inspection of a new wire rope of the same type. In this test, the wire rope is shortened, by at least the removal of the section under test, when the wire rope has a minimum diameter that is, for example, less than 75% of the minimum diameter of a new wire rope of the same type.

In a third test of integrity, the stretch of the wire rope is tested. This test is performed by counting the number of wraps of the wire rope in a given length of wire rope, for example 12 inches. In this test, the wire rope is shortened, by at least the removal of the section under test, when the wire rope has a number of wraps per unit length that is, for example, less than 75% of the number of wraps per unit length of a new wire rope of the same type. For example, a new wire rope might have 20 wraps per foot, and the wire rope might be shortened when it has fewer than 15 wraps per foot.

In a fourth test of integrity, the strength of a single wire of the wire rope is tested. In this test, a single wire, about 1 meter long, of the wire rope is removed from the downhole end of the wire rope. This single wire rope is installed on a pull tester and pulled to destruction. The force required to pull the wire rope to destruction is recorded and compared with the force required to pull a new wire of the same type to destruction. In this test, the wire rope is shortened, by at least the removal of the section under test, when the wire rope has a strength less than 60% of the strength of a new wire rope of the same type.

In a fifth test of integrity, the weight of a wire of the wire rope is tested. In this test, a single wire of the wire rope, for example 12 inches long, is first sandblasted with fine abrasives to remove surface corrosion and contamination. The section of wire rope is then weighed on scales that are accurate to within $1/100^{th}$ of a gram. In this test, the wire rope is shortened, by at least the removal of the section under test, when the wire rope has a weight less than 80% of the weight of a new wire rope of the same type.

In a sixth test of integrity, the single wire tested for weight has its minimum and maximum diameter measured with an electronic caliper. In this test, the wire rope is shortened, by at least the removal of the section under test, when the single wire has a minimum diameter that is, for example, less than 60% of the minimum diameter of a single wire of a new wire rope of the same type.

In a seventh test of integrity, a single wire of the wire rope is tested for resistance to flexing. A 12 inch sample wire from the wire rope under test is clamped in a vise to a pre-selected pressure. A ½ inch spacer having a groove along its length is then placed on top of the vise with the wire lying in the groove. The wire is then gripped with pliers at the top of the spacer and worked by moving the pliers back and forth through a 180° C. arc with constant speed and force until the wire breaks. The number of bends is counted, and compared with the number of bends required to break a single new wire of the same type. In this test, the wire rope is shortened, by at least the removal of the section under test, when the wire survives fewer than, for example, 25% of the number of flexes required to break a new wire of the same type.

In an eighth test of integrity, the twist strength of a wire from the wire rope is tested. In this test, a single wire is tested as in the seventh test, except the wire is rotated until the wire breaks. The number of rotations is counted and compared with the number of rotations required to break a single new wire of the same type. In this test, the wire rope is shortened, by at least the removal of the section under test, when the wire survives fewer than, for example, 25% of the number of rotations required to break a new wire of the same Preferably, testing the integrity of the wire rope comprises performing at least three and preferably all of the tests and the wire rope is shortened when any one of the performed tests fails. However, if the wire rope passes all of the tests, but is marginal in more than one test, for example is within 5% of the fail percentage on, say, three tests, then the wire rope may also be shortened. Again, the decision whether to shorten is economic—a balance of the cost of shortening with the cost of loss of a downhole tool.

All of the test data including the calculated percentages are recorded in an inspection log that is associated with each wire rope. A single sheet or record in a data base may for example correspond to each test. An average of the calculated percentages may be made for each of a succession of tests and the averages graphed as a dependent variable, with time as the independent variable. As the wire rope is used, the average percentage will tend to drop, then when the wire rope is shortened, the average percentage tends to rise, and then fall again as the wire rope is used. The graph may be colour coded. A fail level based on an average of all percentages may for example be 80%, with the graph coloured red up to 80%. A 5% zone from 80% to 85% may be coloured yellow. Above 85% may be coloured green. A wire rope whose average percentage is in the red is shortened, while a wire rope whose average is in the yellow must be watched carefully. A wire rope whose average is in the green is considered acceptable for all uses. More frequent tests and cutting may be needed as the wire rope ages, since the rate of deterioration of the wire rope tends to increase with time.

A summary of averages of integrity tests for a wire rope is shown in the FIGURE. An average of the percentages from the tests is shown on the y-axis. On the x-axis is shown the date of the tests along with the length of wire rope being tested. The length indicated for the wire rope is the length of the wire rope preceding the test. In the FIGURE, tests on the wire rope in August, September and October 2001 reveal that the wire rope does not need to be shortened. On November 9, the wire rope has degraded sufficiently that the wire rope must be shortened, which shows up in the length for November 21 of 3000 m, where the wire rope has sufficient integrity that it does not need to be shortened. In December, the wire rope shows need of shortening again. After shortening to 2700 m, a test the next day reveals that the wire rope needs further shortening and it is shortened to 2500 m.

The test methods described here are suitable for use with an) wire rope used in any industry, but have particular utility in the oil industry. Other tests may also be used, such as an electromagnetic field test determining metallic loss. Immaterial modifications may be made to the invention described here without departing from the essence of the invention.

What is claimed is:

1. A method of protecting against loss of downhole tools in wells, the method comprising the steps of:
    making repeated use of a wire rope to suspend downhole tools in wells, the downhole tools being suspended from a downhole end of the wire rope;
    testing the integrity of the wire rope from time to time according to a maintenance schedule; and
    shortening the wire rope when the wire rope fails integrity testing;
    wherein the testing of the integrity of the wire rope comprises performing a test selected from the group consisting of:
        a visual test of corrosion damage;
        a visual test for broken wires in the wire rope;
        a test of the longitudinal strength of at least one wire from the wire rope;
        a test of the stretch of the wire rope;
        a test of the diameter of a wire from the wire rope;

a test of the diameter of the wire rope;

a test of the flex strength of a wire from the wire rope;

a test of the twist strength of a wire from the wire rope; and a test of the weight of a segment of the wire rope.

2. The method of claim 1 in which the maintenance schedule comprises regular tests of the integrity of the wire rope.

3. The method of claim 1 in which the maintenance schedule comprises monthly tests of the integrity of the wire rope.

4. The method of claim 1 in which testing the integrity of the wire rope comprises a test of the strength of at least one wire from the downhole end of the wire rope.

5. The method of claim 4 in which testing the integrity of the wire rope comprises making plural tests of the integrity of the wire rope.

6. The method of claim 5 in which the wire rope is shortened when the wire rope fails any one of the plural tests of the integrity of the wire rope.

7. The method of claim 6 in which the wire rope is shortened when the wire rope fails a test based on more than one of the plural tests of the integrity of the wire rope.

8. The method of claim 4 in which the wire rope is shortened when the tested wire has a strength less than 60% of a new wire.

9. The method of claim 1 in which testing the integrity of the wire rope comprises a test of the degree of stretch of the downhole end of the wire rope.

10. The method of claim 9 in which the wire rope is shortened when the wire rope has stretched by 25%.

11. The method of claim 1 in which testing the integrity of the wire rope comprises a test of the diameter of the downhole end of the wire rope.

12. The method of claim 11 in which the wire rope is shortened when the diameter of the wire rope is less than 75% of a new wire rope.

13. The method of claim 1 in which testing the integrity of the wire rope comprises a test of the flex strength of a wire from the downhole end of the wire rope.

14. The method of claim 13 in which the wire rope is shortened when the wire rope breaks when a single wire from the wire rope is flexed 25% of the number of times a wire from a new wire rope can be flexed without breaking.

15. The method of claim 1 in which testing the integrity of the wire rope comprises a test of the twist strength of a wire from the downhole end of the wire rope.

16. The method of claim 15 in which the wire rope is shortened when the wire rope breaks when a single wire from the wire rope is twisted 25% of the number of times a wire from a new wire rope can be twisted without breaking.

17. The method of claim 1 in which testing the integrity of the wire rope comprises a test of the weight of a segment from the downhole end of the wire rope.

18. The method of claim 17 in which the wire rope is shortened when the weight of the segment of the wire rope is less than 80% of the weight of an equal length segment of a new wire rope.

19. The method of claim 1 in which testing the integrity of the wire rope comprises performing plural tests selected from the tests listed in claim 8.

20. The method of claim 19 in which testing the integrity of the wire rope comprises performing at least three of the tests listed in claim 8 and the wire rope is shortened when any one of the performed tests fails.

21. The method of claim 20 in which the wire rope is shortened when the wire rope fails a test based on more than one of the performed tests.

22. The method of claim 21 in which the tests are performed regularly.

23. The method of claim 22 in which the tests are performed monthly.

* * * * *